United States Patent [19]

Stade

[11] Patent Number: 4,705,509

[45] Date of Patent: Nov. 10, 1987

[54] POWER SYRINGE WITH VOLUME REDUCING ADAPTER

[75] Inventor: John H. Stade, Ferguson, Mo.

[73] Assignee: Mallinckrodt, Inc., St. Louis, Mo.

[21] Appl. No.: 941,355

[22] Filed: Dec. 15, 1986

Related U.S. Application Data

[63] Continuation of Ser. No. 799,314, Nov. 18, 1985, Pat. No. 4,636,198.

[51] Int. Cl.$^4$ .............................................. A61M 37/00
[52] U.S. Cl. .................................... 604/154; 604/228
[58] Field of Search ............... 604/154, 155, 207–210, 604/228; 128/655

[56] References Cited

U.S. PATENT DOCUMENTS

| | | | |
|---|---|---|---|
| 3,623,474 | 11/1971 | Heilman et al. | 604/155 X |
| 3,701,345 | 10/1972 | Heilman et al. | 604/155 X |
| 3,720,211 | 3/1973 | Kyrias | 604/155 |
| 3,812,843 | 5/1974 | Wootten et al. | 604/155 |
| 3,993,065 | 11/1976 | Szabo et al. | 604/154 |
| 4,006,736 | 2/1977 | Kranys et al. | 604/155 X |
| 4,323,066 | 4/1982 | Bourdon | 604/228 |

Primary Examiner—John D. Yasko
Attorney, Agent, or Firm—Bernard, Rothwell & Brown

[57] ABSTRACT

A syringe for a power injector has an adapter with engaging and gripping means for being secured to the machine grippable protrusion of a backer plate of the piston of the syringe. The rear end of the adapter has a machine grippable protrusion so that the syringe, having its volume reduced by the length of the adapter, can be utilized in a conventional power injection machine.

6 Claims, 10 Drawing Figures

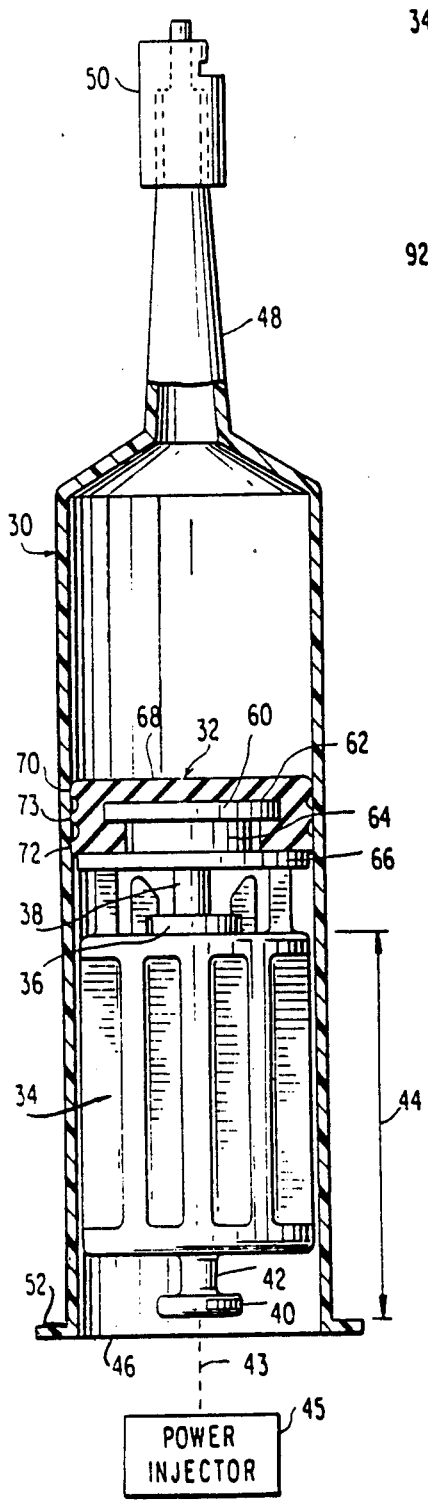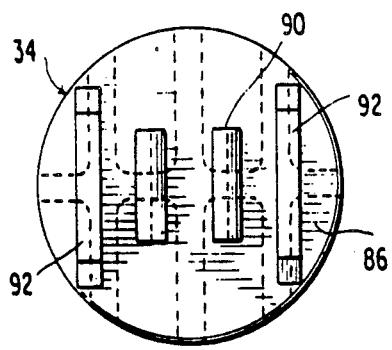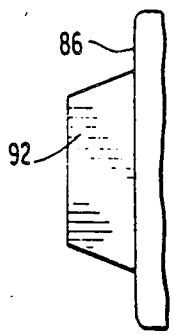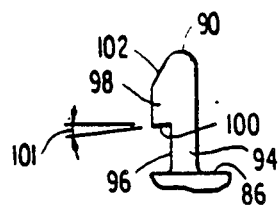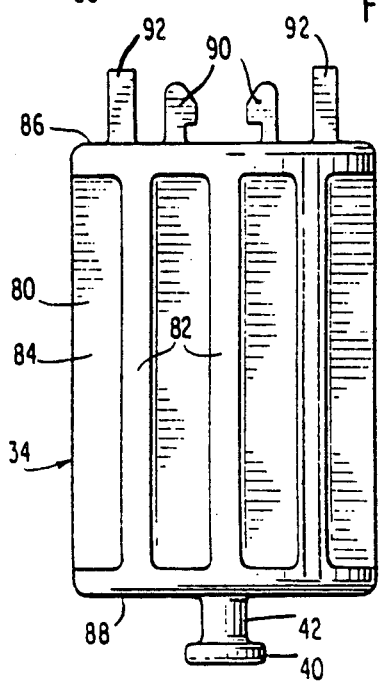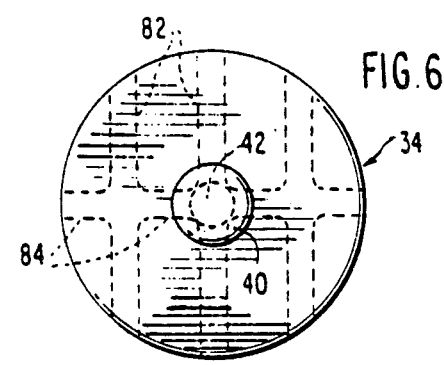

FIG.7
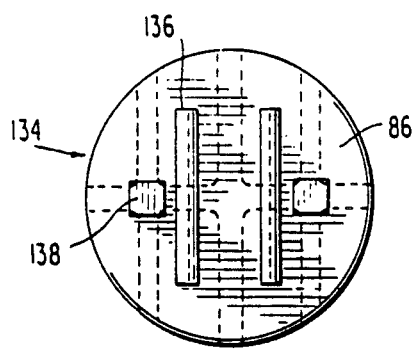
FIG.8
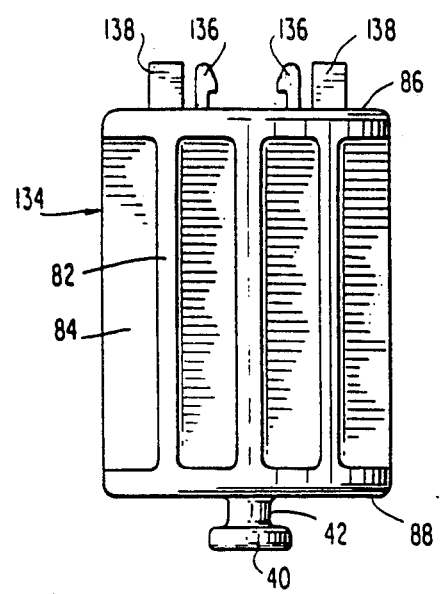
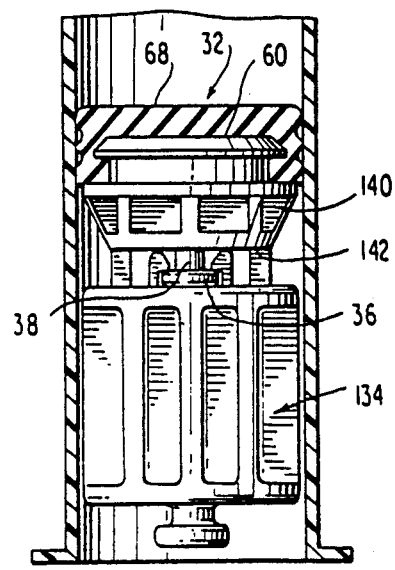
FIG.10
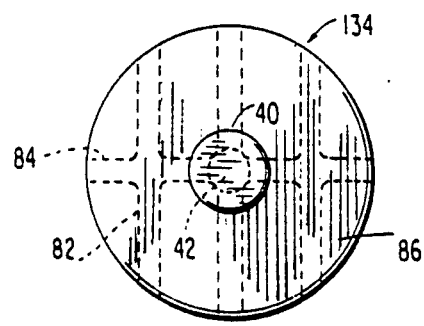
FIG.9

POWER SYRINGE WITH VOLUME REDUCING ADAPTER

This is a continuation of application Ser. No. 799,314, filed Nov. 18, 1985 now U.S. Pat. No. 4,636,198.

FIELD OF THE INVENTION

The present invention relates to syringes for power injection of liquid materials, such as contrast media, into blood vessels to perform uroangiographic procedures

DESCRIPTION OF THE PRIOR ART

The prior art, as exemplified in U.S. Pat. Nos. 3,623,474, 3,701,345 and 4,006,736, contains several power injectors for operating plungers or pistons in syringes to supply liquid contrast media through catheters into blood vessels to enable the producing of X-ray images of organs or blood vessels thereof for medical diagnostic purposes. Generally, the syringes available for a power injector require a relatively large initial volume of contrast media, e.g., 125 or 95 milliliters, to operate properly on the power injector. Often only a portion of contrast media is used, particularly with the newer and more sensitive X-ray and other radiological equipment which is replacing older equipment. Unused contrast media is discarded resulting in unnecessary waste and higher contrast media costs. Existing power injector designs do not allow for their use with partially prefilled syringes.

SUMMARY OF THE INVENTION

The present invention is summarized in a syringe suitable for a power injector wherein the volume of the syringe is reduced by including an adapter having means on its forward end for gripping and engaging the backer plate of the conventional syringe piston and having on its rear end a machine grippable protrusion for being gripped and engaged by the plunger of the injector. The adapter has a selected length extending axially in the open end of the barrel of the syringe for advancing the position of the piston to define a predetermined reduced contents volume.

An object of the invention is to provide a syringe for containing a reduced volume of contrast media and which is suitable for being utilized in existing power injectors.

Another object of the invention is to avoid costs associated with the manufacture, inventory and supply of different syringe sizes.

One advantage of the invention is that power injector syringes having different content volumes can be made from syringe barrels of same size with standard pistons by inserting correspondingly different sizes of adapters which include gripping facilities on the front side for gripping and engaging the backer plate of the piston and which include a machine-grippable protrusion on the rear side thereof for enabling proper operation of the reduced volume syringe by a power injector.

One feature of the invention is that angiography can be performed utilizing a power injector wherein contrast media syringes with smaller volumes of contrast media can be selected, for selected procedures.

Other objects, advantages and features of the invention will be apparent from the following description of the preferred embodiments taken in conjunction with the accompanying drawings.

BRIEF DESCRIPTION OF THE DRAWINGS

FIG. 1 is an elevational sectional view of a syringe for use in a power injector in accordance with the invention.

FIG. 2 is a top view of an adapter in the syringe of FIG. 1.

FIG. 3 is an elevation view, taken from the right side of FIG. 2, of a broken-away upper portion of the adapter of FIGS. 1 and 2.

FIG. 4 is an elevation view taken from the front of FIG. 2, of a broken-away portion including a clip element for securing the adapter to a backer plate.

FIG. 5 is a front elevation view of the adapter of FIGS. 1 and 2.

FIG. 6 is a bottom view of the adapter of FIG. 5.

FIG. 7 is a top view of a modified adapter for use in a syringe in accordance with the invention.

FIG. 8 is a front elevation view of the adapter of FIG. 7.

FIG. 9 is a bottom view of the adapter of FIGS. 7 and 8.

FIG. 10 is a sectional view of a broken-away portion of a syringe containing the adapter of FIGS. 7, 8, 9.

DESCRIPTION OF THE PREFERRED EMBODIMENTS

As shown in FIG. 1, one embodiment of a syringe for a power injector in accordance with the invention includes a syringe barrel indicated generally at 30, a piston indicated generally at 32 within the barrel 30, and an adapter indicated generally at 34. The piston 32 has a rearward machine-grippable protrusion, such as button 36 on stem 38 which is engaged and gripped by the adapter 34. The adapter 34 has a similar machine-grippable protrusion such as button 40 on stem 42 on its rear end for being gripped by conventional piston engaging and gripping facilities (illustrated by dashed line 43) of a power injection machine 45. The length of the adapter 34, as shown by the arrowed line 44 is selected to advance the piston 32 into the barrel 30 of the syringe to define a predetermined reduced amount of volume in front of the piston in the barrel 30. In the absence of the adapter 34, the machine engaging protrusion 36 of the piston 32 generally must be adjacent to the open end 46 of the barrel in order to be engaged by the power injecting machine 45. However, the adapter 34 with its selected length allows the piston 32 to be displaced toward the nozzle end of the syringe by the distance 44 without disrupting the operation of the piston engaging and gripping facilities 43 of the power injector 45.

The syringe barrel 30 is a conventional syringe barrel made of polypropylene or a co-polymer of polypropylene and polyethylene or other suitable material and preferably clear or translucent so that the presence of contents therein can be observed. Additionally, the barrel 30 may have conventional markings (not shown) on the exterior thereof indicating the quantity of liquid within the barrel. The upper end of the barrel 30 has a nozzle 48 with a conventional nut 50 threadably mounted thereon for securing a luer of a catheter (not shown) to the syringe in a conventional manner. While FIG. 1 illustrates the nut 50 mounted on the nozzle 48, the nut 50 can, if desired, be provided as a separately packaged sterilized item. A flange 52 is provided on the open end 46 of the barrel for securing the syringe to the power injector machine 45 in a conventional manner.

The piston 32 includes a backer plate 60 formed of molded rigid plastic with a rear disc-like portion 66, on which the stem 38 and button 36 are centrally mounted, a cylindrical center portion 64 and an expanded forward portion 62. An elastomeric or rubber closure 68 is fitted over the forward portion 62, engaging in the cylindrical center portion 64. The outer edges of the cap 68 have three ringed portions 70, 72 and 73 which form a double seal with the barrel 30.

The adapter 34, as shown in FIGS. 2, 5 and 6, is formed from a molded plastic material, such as polypropylene or other polymer, which is preferably injection molded to the desired shape. The adapter 34 has a body portion 80 which is conveniently formed by a series of ribs 82 and a back plane 84 extending between a front disc 86 and a rear disc 88. The stem 42 and button 40 are formed centrally on the rear disc 88. The gripping facilities for engaging and gripping the backer plate 60 of the piston 32 include a pair of clips 90 and a pair of abutment members 92 extending forward from the front disc 86. The clips 90, as shown in FIG. 4, have a neck portion 94 which defines a recess 96 for receiving the edge of the button 36 and has an enlarged upper or head portion 98 which defines an edge 100 for engaging the forward or top surface of the button 36, as shown in FIG. 1. Preferably, the surface 100 is undercut so as to form an angle 101 inclined downward, for example, 5°, so as to insure that loss of resilience or engagement with the button 36 does not result in an upward sloped surface which can readily release the button 40 upon withdrawal of the adapter. Camming surfaces 102 are formed on tbe upper inner edges of the clips 90 for engaging the edges of the button 36 as the adapter 34 is moved forward against the piston 32 so that the clips 90 are readily flexed apart to permit button 36 to slip past the enlarged head portion 98 and to snap into position within the recess 96 and be held there by the edge 100. As shown in FIG. 3, the abutments 92 have a trapezoidal configuration with a height selected to engage the surfaces of the rear portion 66 of the backer plate concurrently with the engagement of the button 36 by the clips 90. The abutment members 92 are located on opposite sides of the clip members 90 for providing a stable base for power advancement of the piston 32.

A modified adapter 134 illustrated in FIGS. 7, 8, 9 and 10 has portions, identified by the same numerals as the embodiment of FIGS. 1-6, indicating similar structure and function. The adapter 134 contains modified clips 136 for engaging the button 36 of the plunger 32 and has modified abutments 138 mounted on the upper disc 86. The abutments 138 are small rectangular abutments, while the clips 136 are extended longitudinally from the rear to the back so as to accommodate an extended base 140 of the backer plate 60. The extended base 140 of the backer plate 60 is tapered so that the circular surface 142 which engages the modified adaptor 134 has a diameter which is smaller than the barrel diameter. The height of the clips 136 is made equal to the height of the abutments 138 so that the clips 136 can share in the applying and engaging force to the modified backer plate with the tapered extension 140. It is seen that the clips 136 and abutments 138 occupy a smaller circular area of the disc 86 corresponding to the smaller circular surface 142 on the tapered portion 140 of the backer plate.

The present invention provides substantial economic improvements in syringes for power injectors by including an adapter of a selected length to enable the economical production of reduced volume syringes, thus avoiding the cost and waste of unused contrast media that would normally not be used. The employment of the relatively low cost adapters avoids the expense of manufacture and inventory of various sizes of syringe barrels in order to supply power syringes with varying reduced quantities of injection fluid.

Since many modifications, variations and changes in detail can be made to the above described embodiments without departing from the scope and spirit of the invention, it is intended that all matter shown in the foregoing description and shown in the accompanying drawings be interpreted as only illustrating one or more embodiments of many possible embodiments of the invention and as not limiting the scope and spirit of the invention as defined in the following claims.

What is claimed is:

1. An adapter for adjusting the internal volume of a syringe containing a piston having a machine-grippable protrusion thereon, said adapter being a generally elongate body configured for insertion into a cylindrical syringe barrel and comprising:
    (a) a front disc having centrally disposed on one on one side thereof, and extending outwardly from the adapter body, gripping means capable of engaging the grippable protrusion on the pistion to maintain the adapter and the piston in an abutting relationship;
    (b) a rear disc which is disposed coaxially with the front disc, said rear disc having centrally disposed on one side thereof and extending outwardly from the adapter body a machine grippable protrusion; and
    (c) a central body portion connecting said front disc and rear disc.

2. An adapter as claimed in claim 1, wherein the gripping means comprises a pair of clips for engaging and holding the machine grippable protrusion on the piston and a pair of abutment members located on opposite sides of the clips and extending forward from the front disc.

3. An adapter as claimed in claim 2, wherein each of the clips comprises a neck portion defining a recess for receiving the edge of a button on the grippable protrusion of a piston and a head portion defining an edge for engaging a forward surface of such button.

4. An adapter as claimed in claim 3, wherein the head portion of each clip has an inwardly facing camming surface disposed to bear on the edge of the button of a machine grippable protrusion to force the clips apart as the adapter is brought into abutting contact with the piston.

5. An adapter as claimed in claim 1, wherein the machine grippable protrusion extending outwardly from the rear disc comprises a stem having a button affixed to the end thereof.

6. An adapter as claimed in claim 1, wherein the central body portion comprises a back plane and a plurality of ribs extending between the front disc and rear disc, said ribs intersecting the back plane at right angles.

* * * * *